United States Patent [19]

Hossom

[11] Patent Number: 4,693,834

[45] Date of Patent: Sep. 15, 1987

[54] TRANSVERSE FLOW DIAGNOSTIC KIT

[75] Inventor: Miles G. Hossom, Duluth, Ga.

[73] Assignee: Murex Corporation, Norcross, Ga.

[21] Appl. No.: 857,914

[22] Filed: May 5, 1986

[51] Int. Cl.⁴ ............................................. B01D 29/04
[52] U.S. Cl. .................................... 210/767; 210/451;
210/453; 210/455; 210/469; 210/474; 210/477;
210/927; 422/101
[58] Field of Search ................ 422/101; 435/177–182;
436/137, 138, 530, 531; 210/446, 451, 767, 455,
469, 779, 474, 477, 927, 445, 453, 456, 478, 541,
483, 448, 452

[56] References Cited

U.S. PATENT DOCUMENTS 4,623,461 11/1986 Hossom et al. ...................... 210/477

Primary Examiner—Frank Sever
Attorney, Agent, or Firm—Sigalos & Levine

[57] ABSTRACT

The present invention relates to an improved diagnostic device for analyte assay which has a cylindrical body portion and a removably attached cap. The cap has a liquid inlet extending into the cylindrical body portion and has a conical shaped portion leading to a liquid discharge aperture formed therein. A pre-filter may be formed either in the liquid inlet or in a pre-filter container which can be used with the device. The pre-filter container has a substantially cylindrical body which conforms to and can be inserted in the liquid inlet forming part of the removable cap. The container has an open upper end and an associated removable closure, a bottom end sealed with a frangible material and, if desired, a pre-filter positioned in the container between the upper and lower ends. When liquid is placed in the container, the container may be inserted in the liquid inlet and a puncture device associated with the liquid inlet ruptures the frangible material sealing the lower end and allows the liquid to be funneled to a reaction zone on a filter placed beneath or below the discharge aperture. Various size discharge apertures can be formed in the removable caps thereby allowing a particular cap to be associated with a device for a particular test.

26 Claims, 13 Drawing Figures

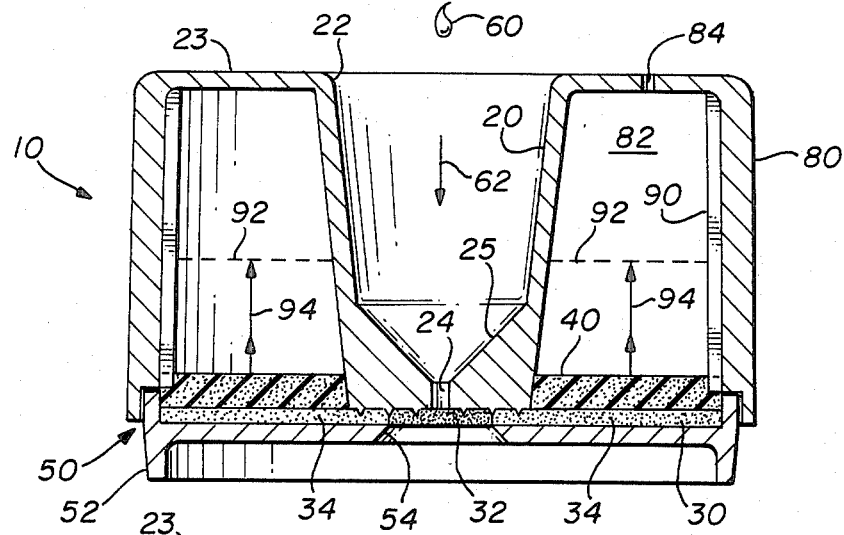
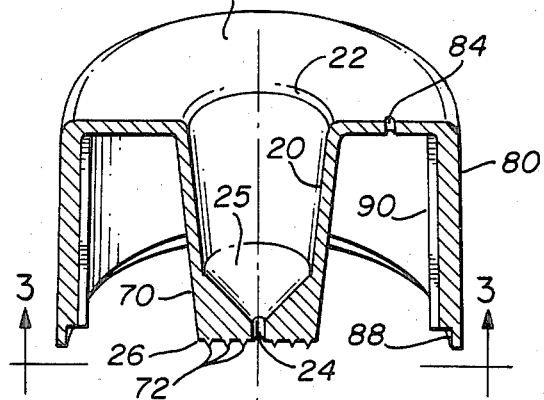
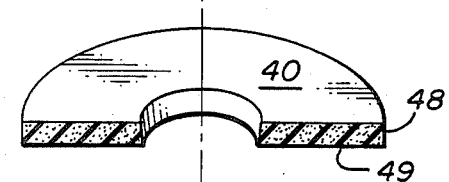
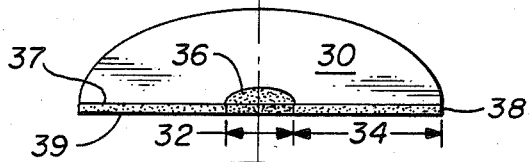
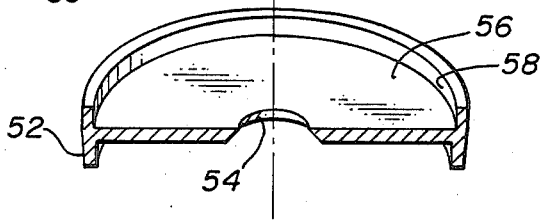
FIG. 1
FIG. 2
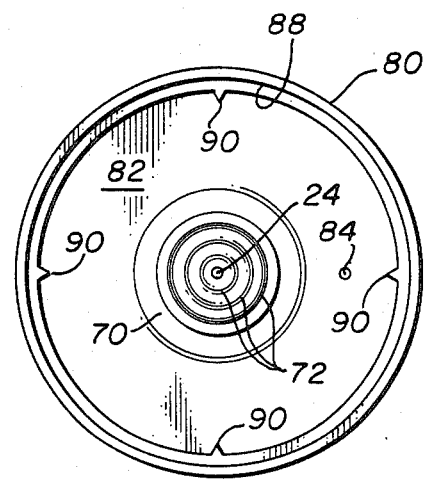
FIG. 3

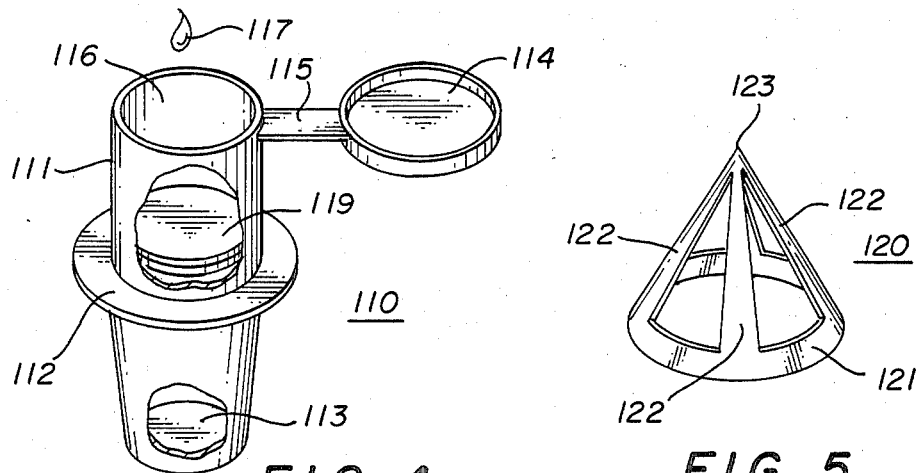
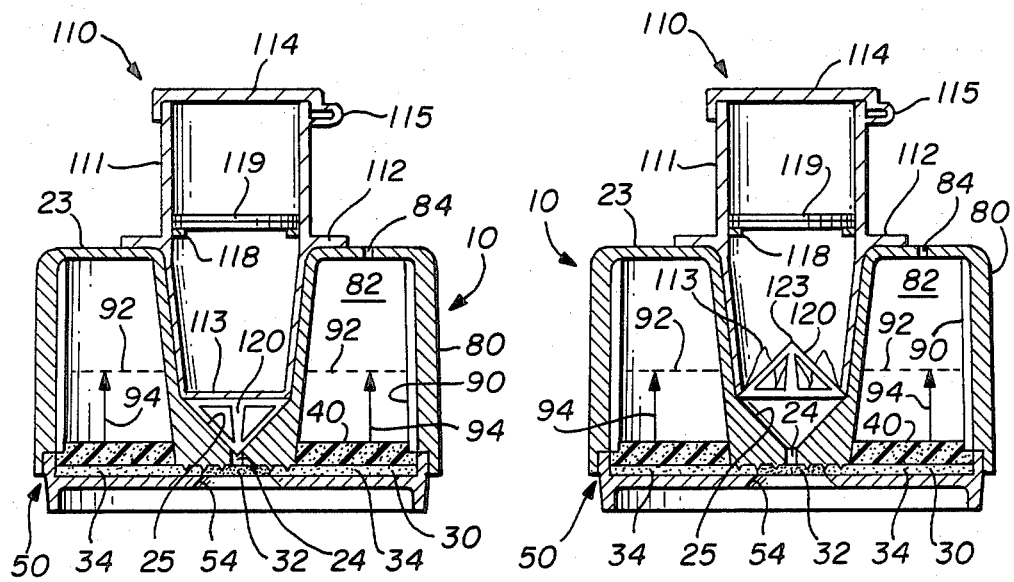
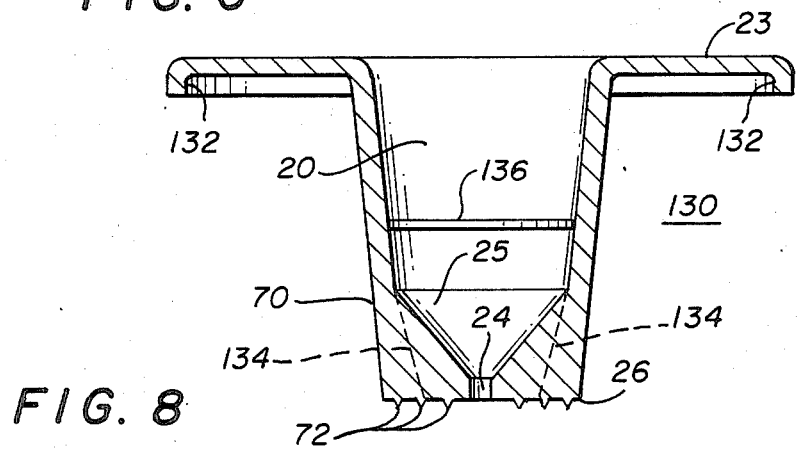

TRANSVERSE FLOW DIAGNOSTIC KIT

FIELD OF THE INVENTION

The present invention relates to an improved diagnostic device for analyte assay which includes apparatus for the separation of a solid phase materials from liquid phase materials. More particularly, the present invention comprises an improved diagnostic device which includes a container for combining fluid and/or solid materials in a convenient, inexpensive manner which can be used to effectively deliver the materials, either prior to, during or subsequent to a reaction, to a filter means in the improved diagnostic device.

BACKGROUND OF THE INVENTION

The present invention relates to improved diagnostic devices for analyte assay. More particularly it relates to improved devices and methods utilizing filter means for testing biological fluids to detect the presence of analytes such as bacterial, viral, parasitic, or fungal antigens and immunoglobulins, hormones, serum proteins, drugs, and the like.

At the present time there are a number of devices and procedures disclosed for diagnosing the presence of such analytes by means of a reaction occurring on filters but they are either too complex, costly, inaccurate, time-consuming or a combination of such factors.

For example, U.S. Pat. No. 3,888,629 discloses a reaction cell having a matrix pad for carrying out immunoassays. The pad serves as the means for retaining the reagents and as the site in which the reaction occurs as one or more of the fluid reagents are added to the pad and pass therethrough to the absorbent material directly below. In addition to the many time-consuming steps required to process the pad to determine the results of the test, including removing it from the device, such device is essentially limited to isotopic tests. It is not practical for nonisotopic tests such as enzyme-linked immunoassays, since the device requires removal of the absorbent pad for viewing. Moreover, certain biological fluids, such as blood sera, contain particulate and/or colored matter which tend to remain on the surface of the matrix pad and thus make it difficult, if not impossible, to obtain an accurate reading in nonisotopic immunoassay procedures. Further, by passing the reagents directly through the entire surface area of the matrix pad there is often poor separation of the analyte since the absobent pad is very thin (thereby affording only a very short distance for a separation to occur) and there is limited concentration of analyte at any location on or in the pad.

Efforts to improve such device are reflected in U.S. Pat. Nos. 4,246,339 and 4,407,943 which try to limit the area of the fiber through which one or more of the reagents must pass. Here again, however, there is flow directly through the thin filter to the absorbent material below the filter resulting agin in poor separation and difficulty in obtaining accurate readings when specimens are being tested which contain particulate and/or colored matter which is retained on the surface of the filter.

The present invention improves the diagnostic device disclosed U.S. Pat. No. 4,623,461, by forming a substantially cylindrical body portion and a removable cap which has a liquid inlet extending into the cylindrical body portion and includes a conical shaped portion leading to a liquid discharge aperture formed therein.

A prefilter may be formed either in the liquid inlet or in a pre-filter container which can be used with the device. The pre-filter container has a substantially cylindrical body which conforms to and can be inserted in the liquid inlet forming part of the removable cap. The container has an open upper end and an associated removable closure, an open bottom end sealed with a frangible material and, if desired, a pre-filter positioned in the container between the upper and lower ends. When liquid is placed in the container, the container may be inserted in the liquid inlet forming part of the cap for the diagnostic device and a puncture device associated with the liquid inlet ruptures the frangible material sealing the lower end and allows the liquid to be funneled to a reaction zone on a filter placed beneath or below the discharge aperture. Various size discharge apertures can be formed in the removable caps thereby allowing a particular cap to be associated with a device for a particular test.

SUMMARY OF THE INVENTION

The present invention represents an improvement over the invention described in U.S. Pat. No. 4,623,461, which is incorporated by reference in its entirety herein. Briefly, the invention as set forth in that application comprises a device for testing a specimen comprising a liquid input means having a receiving inlet and a discharge aperture; filter means positioned below said input means and having at least one reaction zone for receiving liquid from said input means and at least one peripheral zone associated with said at least one reaction zone; absorbent means associated with only said peripheral zone of said filter means; and retainer means for holding said filter means in position below said input mean such that said at least one reaction zone receives liquid therefrom.

The present invention relates to an improved diagnostic device for analyte assay comprising a substantially cylindrical body portion having upper and lower open ends, a filter positioned in said body portion and having a reaction zone and at least one peripheral zone associated with said reaction zone, absorbent means in said body portion and associated with only said peripheral zone of said filter for drawing liquid from said reaction zone to said peripheral zone, a liquid input means removably attached to said upper opening of said cylindrical body portion, said liquid input means having a liquid receiving inlet and a liquid discharge aperture projecting therefrom such that when said liquid input means is attached to said body portion, said liquid discharge aperture is in contact with said filter means reaction zone whereby liquid poured in said liquid input means is funneled for localized discharge only on said reaction zone, and retainer means associated with said cylindrical body portion for holding said filter means below said liquid input means discharge aperture such that said reaction zone receives liquid therefrom.

The invention also includes a reaction reservoir container for removable insertion in the liquid input means receiving inlet, and a support shoulder extending radially and circumferentially about the exterior or the container for resting on the liquid input means when the container is inserted in the receiving inlet thereby holding the container in a secure relationship in the receiving inlet.

BRIEF DESCRIPTION OF THE DRAWINGS

FIG. 1 is a cross-sectional view of the test device of the present invention as disclosed in U.S. Pat. No. 4,623,461;

FIG. 2 is an exploded perspective cross-sectional view of the test device shown in FIG. 1;

FIG. 3 is a bottom view of the dispensing means and a portion of the casing means shown in FIG. 1;

FIG. 4 is an isometric view of a premixing container which can be be used with the test device shown in FIG. 1 or FIG.6 or FIG. 8;

FIG. 5 is an isometric view of a device for puncturing the frangible membrane on the bottom of the premixing container shown in FIG. 4;

FIG. 6 is a cross-sectional view of the test device of the present invention with the premixing container shown in FIG. 4 inserted in the liquid receiving inlet and with the rupturing device shown in FIG. 5 in the bottom portion thereof with the point downward so that the device can be shipped or stored as an integrated unit;

FIG. 7 is a cross-sectional view of the test device of the present invention with the rupturing device of FIG. 5 inserted in the bottom of the liquid input means in a manner in which the points are upward and in which the premixing container shown in FIG. 4 has been inserted in the liquid input receiving means and the frangible membrane on the bottom thereof ruptured by the punctured means thereby allowing any fluid therein to be funneled onto the filter of the test device;

FIG. 8 is a cross-sectional view of the cap for an improved diagnostic device which includes the liquid input receiving inlet and the discharge aperture;

DETAILED DESCRIPTION OF THE DRAWINGS

Figure 9:
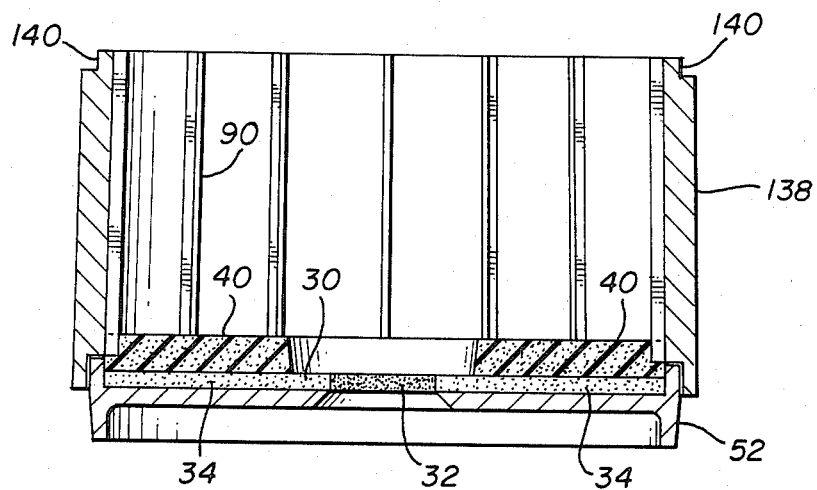
FIG. 9 is a cross-sectional view of the cylindrical body portion of the improved diagnostic device with the retainer portion holding the filter and absorbent means in place in the body portion.

The device of the present invention is suitable for use with any of the conventional procedures used for analyte assays such as isotopic assays and nonisotopic assays such as competitive or non-competitive enzyme-linked immunoassays, enzyme multiplied immunoassays, enzyme inhibition immunoassays, heterogeneous or homogeneous fluorescent immunoassays, chemiluminescent and bioluminescent assays, those assays using labeled RNA or DNA probes, and the like.

The particular analyte assay test to be used will depend upon the particular analyte and the desire of the person carrying out the test. The only essential requirement for each particular test used is that the device of the instant invention be structured, as discussed below, so as to insure that all fluids and reactants necessary to carry out the test are caused to flow outwardly through the filter means from the point of application onto a localized portion of the top surface of the filter to peripheral portions in the filter and that no fluid passes completely through the filter at the point of application. This critical aspect of this invention results in better separation of analyte since it travels further transversely through the filter means, concentration of all the analyte and other reactants at a localized portion of the filter means resulting in more accurate results, and permits top, bottom, and straight-through reading of the filter means to determine the results of the test.

Other than this requirement of the present invention, all of the other steps, conditions, reactants, and the like of the various conventional analyte assays set forth above are those conventionally used in such procedures.

The invention can be more fully understood with references to the drawings in which like numerals represent like elements.

The basic operation of the inventive test device can be understood with reference to FIG. 1 in which the test device 10 comprises a liquid input means 20 with a filter means 30 positioned below said input means 20 and having a reaction zone 32 for receiving the liquid from said liquid input means 20 and a peripheral zone 34 associated with the reaction zone 32. Associated with only the peripheral zone 34 of filter means 30 is an absorbent means 40. Further, there is a retainer means 50 comprised of closure means 52 for holding the filter means 30 in position below the input means 20 such that the reaction zone 32 receives liquid 60 from said liquid input means 20 through discharge aperture 24. Thus, it can be understood that a liquid 60 placed or poured into receiving inlet 22 of input means 20 will flow through discharge aperture 24 into reaction zone 32 of filter means 30. Liquid 60 passes through filter means 30 transversely from reaction zone 32 into peripheral zone 34. A reaction, such as filter separation or immunological binding, may take place in the reaction zone 32 as the liquid is diffused therethrough. The color changes or other reaction reading signals produced in the reaction zone 32 can be viewed or read either from the bottom of the device through viewing port 54 in closure means 52 or from the top of the device through discharge aperture 24. The remaining liquid is absorbed by absorbent means 40 which is in contact only with the peripheral zone 34 without directly contacting reaction zone 32. Thus, the liquid passes through reaction zone 32 before being absorbed. The absorbent means 40 is positioned within hollow cavity 82 formed within casing means 80 which is removably or permanently press-fit onto closure means 52. As liquid is absorbed by absorbent means 40, air within hollow cavity 82 is displaced by the liquid. The displaced air escapes through vent 84 so that air pressure is equalized. All components other than filter means 30 and the absorbent means 40, the construction of which will be described below, may be formed of any suitable inert material such as molded polystyrene or other plastic material. The material is preferably opaque and preferably white in color so that color interference with the reaction signal is reduced. In addition, while the shape of casing means is shown to be substantially cylindrical, it may have other shapes such as square, octagon and the like.

The amount of liquid used depends upon the test, assay or immunoassay being performed. In any given test more than one type of liquid may be used in a predetermined sequence. For example, a fluid may be used to prepare the reaction zone, then a washing fluid or solvent added, then a bodily fluid specimen and then another washing liquid added, then a reaction indicator fluid or coloring agent added and then another washing fluid added. The capacity of the absorbent means must be sufficient to handle all the liquid used in the test. The large volume of the inventive device allows the user added flexibility in the test which can be performed. Also an inert reaction zone 32 can be used because the device has sufficient capacity for preparatory additions of liquid to form an active reaction zone.

The liquid input 60 into the liquid input means flows in liquid flow direction 62. It will be understood that in the preferred embodiment the motivating force of the flow is gravity such that the liquid flows through input means 20 generally from top to bottom or from receiving inlet 22 to discharge aperture 24.

The liquid flows through discharge aperture 24 onto filter means 30 positioned below input means 20. Filter means 30 has at least one reaction zone 32 for receiving liquid from said input means. Also filter means 30 has at least one peripheral zone 34 associated with the reaction zone 32. The diameter of discharge aperture 24 may be variable but is sufficient in connection with the liquid pressure head present in input means 20 for a particular test so that the liquid will discharge onto upper surface 37 of filter means 30 and will not be forced straight through the filter 30 and out the bottom surface 39. Thus, the hydrostatic pressure is adjusted so that the liquid enters the filter by gravitational forces and it is diffused through the filter 30 by capillary action. It has been found that, for an input funnel 20 which is approximately 1.2 inches high and a filter 30 which is 0.03 inches thick, a discharge aperture 24 having an approximate diameter of 0.06 inches is sufficient for most tests. Absorbent means 40 acts to ensure the outward fluid flow so that no liquid goes completely through filter means 30 at the point of application from input means 20. Thus, the diameter and height of the discharge aperture 24, type and thickness of filter means 30, and type and thickness of absorbent means 40 are correlated to ensure that no liquid used for any particular assay will be passed straight through the filter, but will travel transversely outwardly from the point of application in the filter plane. The particular dimensions for each assay procedure can be readily determined by routine experimentation.

A unique aspect of the present invention is the combination of the pushing force of gravity and the outward transverse pulling force of the capillary action of the filter means 30 and absorbent 40. Other devices commercially available make use of predominantly either only a pushing force or a pulling force. Examples of such devices are those that drop fluids onto the filter via a pipette, relying on a "radial" flow of fluid through the filter, or a reservoir means whereby a column of fluid is drawn straight through the filter without any transverse flow of fluid along the plane of the filter. The present invention employs both forces so that a column of fluid is pushed onto the filter by hydrostatic pressure, and subsequently drawn by capillary action outward through the filter from the point of application to a peripheral zone and then into the absorbent means. The use of these motivating forces effects a more rapid and complete filtration and separation of components in the filter means.

In the preferred embodiment the filter means 30 is made of a porous material capable of drawing liquid within its structure by capillary action. The pores of the filter 30 should be sufficiently small to effect a filter separation of an insolublized component within the liquid from a solublized component. The filter may be composed of materials such as glass fiber filter paper, nitrocellulose, plastic, synthetic polymer, cellulose, cellulose acetate, polytetrafluoroethylene, polyethylene, polypropylene, polyvinylidene fluoride, or any other material formable into a filter having the qualities and characteristics as described above. In many applications it is desirable to use a material which is inert and chemically nonreactive with the analytes and washing solvents with which the test device is to be used. It has been found that a filter means, which comprises a microporous membrane having substantially uniform pores between 25 nanometers and 25 micrometers, has the characteristics described and is useful in performing immunoassay testing procedures for which this device is particularly useful. Examples of filters which may be used include filter paper known as WHATMAN GF/D and filter discs made by MICRO FILTRATION SYSTEMS of borosilicate glass known as GD-120 standard filter discs.

The apparatus of the present invention is beneficial where chemical reactions (typically the immunochemical reactions) occur external to the device and the final reactants fed into the filter means for separation of the unreacted elements therefrom. In external reactions, improved accuracy of component addition is possible. It is generally accepted that a longer incubation period can afford more complete reaction and binding of the reactants, thereby increasing the sensitivity of the assay. Systems that conduct the reactions solely within the filter means frequently are limited in the length of the incubation period. The filter can dry out during long incubation periods with such systems decreasing the sensitivity of the assays. In the present invention, because the reactions can take place externally to the device, much greater control and flexibility are obtained over the incubation period, greatly improving the overall sensitivity and specificity of the assay. In such instances the diagnostic device is used primarily as a separation device to separate soluble components from insoluble components within the liquid specimen poured into the input 20 of the inventive test device 10. Thus, where it is desirable to perform numerous and varied assays without having a specific device for each specific assay, the inventive test device is useful. Such a nonspecific device may be composed of inert materials and therefore may be stored for an indefinite period of time and without refrigeration. Moreover, such nonspecific devices can be produced using mass production techniques at substantial cost savings.

The device 10 may also be used for specific immunochemical assays by "prespotting" the reaction zone with an analyte specific reactant. Prespotting is a term used to indicate that in a localized region 36 of filter means 30, such as within reaction zone 32 only, specific analyte reactant may be immobilized on the internal surfaces of the filter material. These internal surfaces define the interstices within the structure of the filter material. In prespotting, the reaction zone 32 of the device is prepared for direct use of a test specimen often without preparatory additions to the test device. For example, the manufacturer of the device could place in the filter reaction zone a binding protein to which an antibody is bound, which antibody is immunologically reactive with a specific antigen. Thus, a specimen being tested for the specific antigen would be poured into the test device inlet, flow through the discharge aperture and would be discharged onto the upper surface 37 of reaction zone 32 of filter 30. The solution would be pulled by a wick through the reaction zone 32 which has been prespotted at 36. After a sufficient incubation time, a washing solution would be added to the device and is again washed through the reaction zone, washing unreacted components of the specimen outward into the peripheral zone, and into the absorbent means, thus stopping the immunological reaction. If the specific antigen is present in the specimen, it binds to the antigen's specific antibody which itself is already immobilized within the filter and would remain in the reaction zone after the washing step. The unbound antigen and other material within the solution are effectively washed away from the reaction zone and into the absorbent means 40. Finally, an antibody labeled with a detectable signal/label, such as an enzyme which generates a particular color of light, is poured through the test device and binds to the bound antigen. A washing solution is again needed after a desired incubation period to remove all unbound enzyme labeled antibodies. Then the reaction zone is viewed through the viewing port 54 to determine if the color produced by the enzyme is present and, if so, in what amounts. The presence of the enzyme indirectly indicates that the antigen was indeed within the sample specimen. The absence of the enzymes indicates no antigen was present.

As shown in FIG. 2, the preferred embodiment of the test device is formed substantially symmetrically around a vertical axis. The absorbent means 40 is a skirt 40 of absorbent material which entirely surrounds the discharge aperture 24 of the input funnel 20. The absorbent material may be any suitable material such as hydrophilic polymers, particulate absorbents, glass fiber, cotton fiber, cellulose fiber, wood pulp, or sponge material. In the preferred embodiment a compressed sponge material is used which expands upon absorbing liquid. In other embodiments of this invention absorbent means 40 may be positioned partially encompassing the periphery of reaction zone 32 as shown, for example, in FIGS. 7, 8, and 9.

The filter means 30 is formed in a flat circular disc shape. The closure means 52 is of a size and shape corresponding to the filter means 30. This configuration promotes uniform flow outwardly from the point at which liquid is discharged from discharge aperture 24 and onto reaction zone 32. The uniform flow outwardly through filter 30 as provided by this inventive test device is advantageous over other test devices for several reasons. It is desirable to have all of the specimen pass through a localized zone of the filter material, and to have relatively large quantities of liquid pass through the localized zone. This is accomplished by making the receiving inlet 22 larger than the discharge aperture 24 so that large quantities of liquid are funneled for localized discharge onto the reaction zone 32. The outward flow permits a large area of absorbent material to be in contact with the filter so that large quantities of liquid can pass through the filter means while maintaining a small reaction zone. Further, to promote the passage of the liquid through the reaction zone rather than merely spreading across the surface of the filter, a substantially liquid impermeable shield 70 contacts the surface of the filter means 30 separating the discharge aperture 24 from the absorbent means 40.

It is important that fluid applied to the reaction zone area pass into the filter means and flow outwardly into the absorbent means. Flow of fluid across the top of the filter means must be impeded so as to ensure the chromatographic separation of the bound from unbound materials via capillary action. As shown in FIG. 2, the shield means 70 is provided by abutting the bottom end 26 of the liquid input means 20 against the filter means 30. The shielding action is promoted by having at least one serration 72 which contacts the upper surface of the filter means and compresses it slightly to provide an impediment to surface flow so that the liquid is directed into and must pass through at least a portion of the reaction zone 32 structure via the interstices within the reaction zone of the filter means 30. To promote complete shielding with minimum localized compression of filter means 30, multiple serrations are used in the preferred embodiment as shown in the drawings. Alternatively, the shield means 70 can be permanently affixed to the filter means, ensuring the separation of the discharge aperture from the absorbent means.

A unique aspect of the present invention is the ability to read and illuminate from either the top or bottom surface. Other systems are limited to reading the reaction from either only the top or bottom surface and typically require illumination from the same side as it is being read; these include filter discs, dipsticks, tabs containing filter materials, devices where the illumination opening and the reading opening are the same, etc. The capability of reading from either surface enhances the flexibility and adaptability of the present invention to different reaction systems and analyzing instruments. A beneficial aspect of the inventive test device is that the reaction zone can be viewed from the bottom. As shown in FIG. 2, closure means 52 has formed therein a viewing port which is held in alignment with the reaction zone of the filter means. In the embodiment shown the filter means 30 is a flat circular disc shape, the absorbent means 40 is in the shape of an annular ring, and the reaction zone is a circular disc shape. The viewing port 54 permits easy viewing of the bottom face 39 of the reaction zone 32 without interference or obstruction caused by either the input means 20 itself, or by debris and particulate or colored matter which may have been present in the liquid specimen. It is especially advantageous to have a device which permits bottom reading where the liquid specimen comprises bodily fluids such as blood, urine, feces, mucus, or other specimens which may be colored or in which contaminants may be present. Such contaminants include colored red blood cells, dead cellular materials from mucosal specimens, various colored debris, and food particles from feces, crystalline or other precipitates from urine, etc. The prior art devices require that the samples be cleansed of particulate matter as by centrifuge devices prior to testing. Viewing port 54 is made sufficiently large to allow light to enter so that an accurate reaction reading can be made. The test device is versatile and the reaction can also be ready by illuminating the top surface and reading from same through liquid input means 20 where such a reading is desirable, as where the sample specimen is relatively free of particulate matter or as where the particulate matter entrapped near the upper face of the reaction is of particulate importance to the test. Moreover, with the present test device it is possible to illuminate from the top surface and read the bottom surface, or illuminate the bottom surface and read from the top. This unique ability permits convenient instrument reading of samples by measuring the absorbance of light by material present in the filter. An assay particularly well suited for this is an enzyme substrate system whereby the density of substrate as related to the presence of analyte is measured by the increased absorbence of light passing through the filter. Since a reading can be made from either surface, the advantage is in its adaptability to different instruments.

The liquid impermeable shield 70 can be designed to enhance the readability of the reaction by having the bottom surface of the shield be either light absorbent, light reflecting, or light transmitting, depending on the desired method of reading the reaction. For example, where it is desired to both illuminate and read from the bottom surface, a reflection surface at which light received through the filter will reflect off the sample and exit the bottom surface, thereby enhancing readability of the reaction. When it is desirable to eliminate reflection, reading through the filter by illuminating the opposite surface can be enhanced. By designing the shield to be light transmitting in this manner the instrument reading can be improved.

As can be seen with reference to FIG. 2, enclosure 52 provides a flat surface 56 to support the substantially flat bottom face 39 of the peripheral zone 34 of filter means 30. Also alignment means 58, which may be a circular ridge 58 integrally formed on holding means 52 has an inside diameter corresponding to the outside diameter 38 of filter disc 30 and an outside diameter corresponding to the inside diameter of lip 88 of casing 80. Likewise, absorbent means 40 has an outside diameter 48 corresponding to the outside diameter 38 of filter means 30 and the inside diameter of alignment means 58. Thus, all the component parts of the invention are fitted together and held in alignment. In particular, the reaction zone 32 is held aligned with discharge aperture 24 for receiving liquid therefrom. Alignment of the reaction zone and the discharge aperture is crucial for accurate reproducible results. The funneling means consistently delivers fluid precisely to the same position on the filter via the discharge aperture, thereby eliminating random positioning errors by manual manipulations or mechanical means. The accurate positioning of fluids onto substantially the center of the reaction zone affords greater accuracy in results. Where the reaction occurs external to the device, all fluids added to the device are guaranteed to be applied to the same point because of this alignment. Furthermore, where the filter is prespotted with a component, such as an antibody, accuracy is ensured by the correct addition of antigen and wash fluids precisely to the prespotted area. Other devices introduce user error by not having a fluid delivery system funneling means aligned with the reaction zone of each device. Some other systems have a large area of filter containing a small reaction zone whereby a user must approximate where the colorless prespotted component is located. If not located precisely in the center, incomplete binding or washing can occur, reducing the overall accuracy and sensitivity of the assay.

The upper face 37 of the filter 30 will trap color or particulate matter contained within the specimen and prevent such insoluble matter from reaching the bottom face 39 of the reaction zone 32. Only the soluble material will diffuse outwardly through the filter and down to the bottom face 39. The reading port 54 as described above is held in alignment with the reaction zone to afford a reaction reading signal that is free from false coloration or extraneous matter.

To provide maximum separation of bound from unbound label components and thereby reduce background noise during observation of the reaction, the invention provides for outward diffusion of liquid applied to the filter toward the absorbent material 40. The filter material 30 serves not only as a means for trapping and immobilizing particulate matter and reaction components, but also as a means for liquid transfer from the point of application to the absorbent material 40 so as to effect a filter separation. Diffusion of the material outward from the center point of application rather than directly down through the filter provides a more effective separation, particularly during the washing step where the unbound components are to be removed from the bound components. Properly performed in the present inventive apparatus, an assay procedure will leave a concentrated spot of bound label in the reaction zone 32 of the filter material, and immediately surrounding the reaction zone 32 will be clear peripheral zone 34 containing negligible signal generating material, and the unbound label will be washed away from the observation area of the reaction zone.

To maximize the contrasting zones, relatively large quantities of washing solution are required. To promote effective transfer of the relatively large quantity of liquid from the peripheral zone 34 to the absorbent means 40, the annular ring 40 of absorbent material is held in intimate contact with a portion of peripheral zone 34. A large transfer area can be accomplished by forming the annular absorbent ring in the shape of a hollow cylinder of substantially uniform thickness having a flat base 49 which is held in intimate contact with the upper face 37 of the peripheral zone 34 of the filter means 30. Continuous and complete contact is promoted by forming at least one, and preferably more than one, evenly-spaced projections 90 on the internal surface of cavity 82. Frictional contact between absorbent means 40 and projections 90 acts to restrict the movement of absorbent means 40 upward into the hollow cavity 82. Thus, it is held in intimate contact with the filter surface for direct transfer of liquid therefrom.

Where the hollow cylinder absorbent material is compressed sponge material, it will be relatively rigid in its dry state and will become flexible upon absorbing liquid and expanding. The additional flexibility permits the absorbent material to expand deforming slightly to accommodate projections 90 as it expands into hollow cavity 82. The air displaced thereby is permitted to escape through vent 84. As shown in FIG. 1 by dashed lines 92 and directional arrows 94, the compressed absorbent material may expand several times its original thickness upon absorbing the substantial amount liquid used in the testing device.

The absorbent material makes possible the use of a very large volume of wash fluid. Generally, a more effective separation is obtained when using large wash volumes. In other devices not containing absorbent material, the amount of wash solution that can be used is limited by the absorbent characteristics of the filter material, typically much less than an absorbent material such as a sponge or compressed wood pulp material.

As shown in FIG. 4 sample container 110 comprises a substantially cylindrical hollow tube means 111 having a liquid input means 116 at the top end and a substantially flat liquid impermeable or semi-permeable closure means 113 at the bottom end. Surrounding and permanently affixed to or integrated with the outside of tube means 111 is a substantially flat radially extending flange support means 112 for supporting the sample container 110 when positioned within the open end of the test device 10 as shown in FIG. 6. Materials such as fluid 117 can enter the sample container 110 through liquid input means 116 and react within the container. In an alternative embodiment it may be desirable to axially affix to or otherwise be supported by a circumferential ledge 118 on the inner wall of tube 111 a semi-permeable filter 119 for prefiltering the reaction components, such as where a feces specimen containing undesirable solid particles (e. g. food or red blood cells) is to be assayed. A removable top closure means 114 may be employed to cover top end 116 such as where the contents of sample container 110 are to be shaken, mixed, vortexed or otherwise agitated. Closure means 114 may be a nonaffixed cap or cover or can be attached to tube means 111 in proximity to liquid input end 116 by a flexible joint means 115. Cover means 114 will provide a tight seal over tube 111 yet be removable by the user, if desired.

Sample container means 110 is sized as to removably fit within the liquid input means 20 (shown in FIGS. 1, 6, 8, and 10) of test device 10 by supporting the underside of flange 112 on the upper surface 23 surrounding receiving inlet 22. This permits the stable positioning of sample container means 110.

Puncture means 120 (shown in detail in FIG. 5) is suitable for use where the bottom end 113 of container 110 is a thin frangible surface or membrane covering tube 111. Puncture means 120 comprises a base 121 with at least one arm 122 forming a relatively sharp point 123 capable of piercing the bottom surface 113. Where several arms 122 are used, they join together in a conical shape to form a single sharp point 123.

As can be seen in FIG. 6, puncture means 120 is positioned in conical portion 25 in the lower portion of liquid input means 20 with the point downwardly. The container 110 can then be placed on top thereof for storage purposes without the bottom frangible portion 113 being ruptured. This requires of course that the puncture means 120 be formed in a substantially conical shape which conforms to conical shape 25 in the lower portion of the liquid input means 20. However, this configuration is advantageous inasmuch as it allows all of the components of the test device to be kept together for shipment and or storage purposes.

When it is desired to utilize the test device 10 in performing a test, the puncture means 120 is removed and replaced within the lower portion of the liquid input means 20 with the point 123 facing upward toward the frangible bottom end 113 of container 110.

As can be seen in FIG. 7, as pressure is applied downwardly on container 110, points 123 are forced into intimate contact with bottom end 113 of container 110 piercing it, and thereby enabling the contents of container 110 to exit bottom end 113 and into test device 10 to be channeled by discharge aperture 24 onto reaction zone 32 of the filter 30. Various embodiments of puncturing means 120 are possible such as, but not limited to, an array of spikes or protrusions supported by base 121 or an inverted hollow conical shape with the pointed end directed upwards and the surface of the conical shape perforated with at least one perforation to permit the passage of fluid therethrough.

The sample container 110 has a number of different functions which act to enhance the versatility and efficiency of the test device. By adding the sample and reactants to the container 110 without the filter means 119 therein, it becomes a reaction vessel with the capability of being agitated to facilitate reaction kinetics, as well as permitting extended incubation. In circumstances where a filter would dry out over a relatively long incubation period where the materials are reacting on or within the filter, a means for "off-line" incubation presents significant benefits. Control and flexibility of reaction times is increased by using such a sample container 110. It can also be used as a specimen extraction processing container by enabling the user to pretreat a specimen prior to introduction to the reaction zone.

Semi-permeable membrane or filter 119 can be employed as a pre-filter means in container 110 whereby a specimen containing particulate matter may be pretreated to reduce the possibility of clogging reaction zone 32 of filter 30 with undesirable material. The membrane 119 can also be pre-impregnated or otherwise have immobilized on or within its pores reagents useful in a particular assay format or interest, so that materials added to the sample container 110 would come in intimate contact with the immobilized reagent while passing through membrane 119. Alternatively, reagents can be insolublized, such as by lyophilization, on the inner walls of the container 110 which would become resolublized upon addition of fluids to the sample container 110. Either method would save the user time by reducing the number of stages in the assay procedure. Spillage is also reduced by having fewer reagents to manipulate.

While a liquid input means that is integrally formed with device 10 as shown in FIG. 1, FIG. 6 and FIG. 7 provides maximum compactness of form, as well as other important advantages, a removable liquid input means 130 as shown in FIG. 8 presents certain improvements and advantages over the prior art. Input means 20 in FIG. 8 still functions as a funnel means to concentrate liquids (i. e. reagents, specimen, and the like) onto the reaction zone 32 through discharge aperture 24. In order to achieve maximum efficiency of component separation on or within the filter it is important that the liquid discharge aperture 24 be in contact with filter means 30. As previously described in relation to FIG. 1, at least one serration 72 contacts the upper surface of the filter means 30 compressing it slightly to provide an impediment to surface flow of liquid. This feature is retained in the present invention as shown in FIG. 8 wherein the liquid barrier 70 can have at least one, and preferably multiple, serrations 72 designed and formed on it. The slight compression may occur sufficiently by simply having the container 110 resting in cap 130 in the test device 10 in a manner similar to that shown in FIG. 7, whereby its own weight provides the pressure required. Preferably, however, cap 130 is detachably affixed to test device 10 by any suitable means such as, but not limited to, screw threads 132 or may utilize other known methods of attachment such as snap-fit, slot-fit, groove, pressure-fit, breakaway, and the like. The only requirements include convenient removal of the cap or input means 130, and secure and consistent positioning of discharge aperture 24 in contact with reaction zone 32 while maintaining the slight compression of the filter means 30 by at least one serration 72. Many possible affixing means are possible and are readily adaptable to plastic molding and manufacturing techniques.

With a removable cap 130 having input means 20, a greater portion of the area surrounding reaction zone 32 may be made visible by varying the size of discharge aperture 24 as indicated by dashed line 134. This feature enables a user to compare any positive reaction product present in the reaction zone 32 to the area immediately surrounding reaction zone 32 which contains no reaction product. In the case of instrument measurement, a lens could be positioned closer to the filter mans 30 than otherwise possible when the reaction zone 32 is receiving liquid.

By having a removable liquid input means or cap 130, the utility of using differently sized discharge apertures 24 becomes significant. Different assay procedures and different analytes typically require some optimization of the rate at which reagents and sample are added to the reaction area. A discharge aperture of a given diameter possesses particular flow dynamics for a given liquid density and quantity. It is desirable to control this flow rate in a test device such as the one disclosed, and, having the option to use one of several different liquid input means or caps 130, each possessing a particular aperture diameter, gives the user much greater flexibility in optimizing the performance of an assay.

Additionally, a removable liquid input means or cap 130 allows for the use of one aperture size for applying liquid to the filter means 30 and, when cap 130 is removed, a cap 130 with a different aperture size can be used transmitting light to the filter means 30 for reading the reaction products; therefore, greater sensitivity of measurement may be obtained.

A filter membrane 136 can be placed within the liquid input means or cap 130, if desired, to serve as a pre-filter means before addition of the liquid material onto the reaction zone. In a manner similar to the pre-filter membrane 119 of the sample container 110 discussed previously, such a pre-filter means 136 can be removably or permanently associated with the liquid input means or cap 130 and may or may not have materials pre-spotted on or within the membrane. This feature would enable a user to pour in samples that may contain particulate or crystalline matter that might otherwise clog the reaction zone 32 of filter means 30.

As can be seen in FIG. 9, the substantially cylindrical body portion 138 has attached to it in the manner described previously in relation to FIG. 1, retainer portion 52 which holds filter 30 and absorbent means 40 in their proper relationship with respect to cylindrical body 138. On the upper end of body portion 138 are threads 140 which match with threads 132 on cap 130 shown in FIG. 8. Thus cap 130 can be placed with liquid input means 20 extending into cylindrical body portion 138 and then cap 130 is rotated to mate threads 132 with 140 for attachment or may be attached in any other well known manner as set forth previously.

Figure 10:
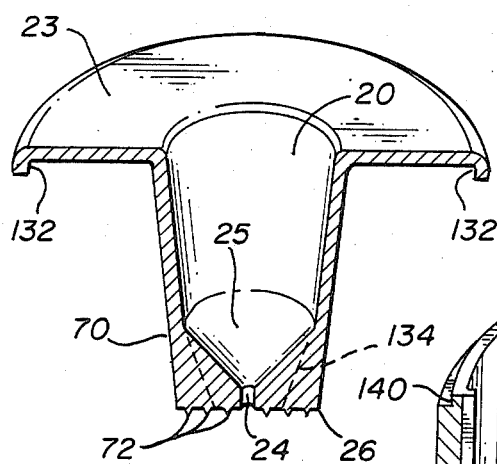
FIG. 10 is an isometric cross-sectional view of the cap illustrating the liquid input means and the liquid discharge aperture.
Figure 11:
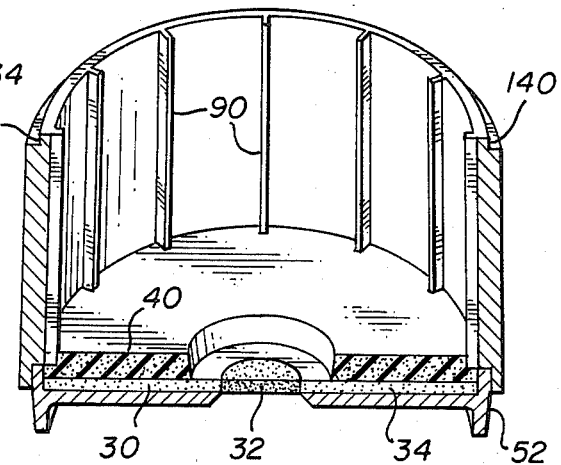
FIG. 11 is a cross-sectional isometric view of the body portion with the retainer portion holding the filter and absorbent means in place and illustrating threads on the upper portion of the cylindrical body portion to which the cap in FIG. 8 and 10 can be removably secured with mating threads.

FIGS. 10 and 11 are cross-sectional isometric views of cap 130 and cylindrical body portion 138 shown in FIGS. 8 and 9. FIG. 10 is an embodiment which does not include the filter 136 shown in FIG. 8 but it obviously could be included if desired. Device 10, reaction container 110, puncturing means 120, cap 130, cylindrical body portion 138 and retaining means 52 could be formed of any suitable inert material such as molded polystyrene, polyethylene or other plastic materials. The walls of container 10 may be either rigid or flexible. Further, as stated previously, cap 130 maybe removably associated with cylindrical body portion 138 by detachably securing it in a well known manner such as by snap-fit, screw threads, pressure-fit, grooves, breakaway portions, or any other well known fastening means.

Figure 12:
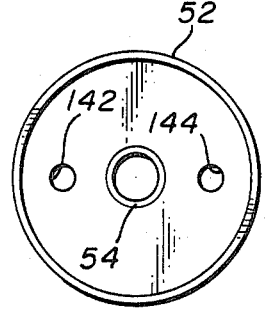
FIG. 12 is a bottom view of the closure or retainer means illustrating the center viewing port as well as two additional ports spaced from the center viewing port for the purpose of detecting when improper washing has occurred during the testing.

FIG. 12 is a bottom view of the closure or retainer means 52 illustrating a modification thereof in which viewing ports 142 and 144 are formed in addition to the center viewing port 54. This embodiment provides enhanced visual comparison of the reaction zone 54 and any color developed therein with a white negative background. Where color forms in the ports outside of the reaction zone, improper washing may have occurred. Without control ports 142 and 144, even if no reaction products are present to cause a particular reaction color to be visible in port 54, there may be, without proper washing, a reaction color caused by products other than the desired test product in the sample being tested. If that is the case, a false color may show up in center viewing port 54 indicating a positive test when in fact it is a negative test. By the use of additional control ports 142 and 144, improper washing can be detected. If a negative reaction actually exists in center viewing port 54 and proper washing has occurred, then no color will exist in center viewing port 54 or spaced ports 142 and 144. If a positive indication shows up in center viewing port 54 only because of improper washing, that same reaction indication will appear in spaced ports 142 and 144 thus indicating that there has been an improper washing. If there is a positive reaction in center viewing port 54 with proper washing, then no reactions will show in spaced ports 142 and 144. Thus a step of improper washing can be detected by the use of additional ports 142 and 144 so as to distinguish a false positive reaction in center viewing port 54 from a true positive reaction.

In addition, the embodiment shown in FIG. 13 can be used where again, first and second additional spaced ports 142 and 144 are used to detect improper washing as described in relationship to FIG. 12. In addition however in FIG. 13, a third spaced port 146 is added which is a control standard port. This location is treated in any conventional manner so as to produce a visibly colored reaction when substrate solution is added thereby acting as an internal control. This would indicate, regardless of the presence or concentration of analyte, that the proper assay procedures have been followed. For example, if a pregnancy test were to be conducted, the filter pad would have HCG immobilized at the location of third viewing port 146. Addition of the enzyme linked antibody and subsequently of the substrate will cause a color change (a positive reaction) as port 146 which in fact it should have if the proper immunoassay procedure has been followed. If then the same color reaction shows up at center viewing port 54 after the substrate solution is added then the positive test is confirmed. If no color appears in center viewing port 54 but a color is present in third port 146, a negative test is confirmed. In addition, of course, ports 142 and 144 would again remain clear with no reactions if proper washing has taken place. If improper washing has taken place then again these ports 142 and 144 would show a reaction which would mean that the test would have to be redone.

Figure 13:
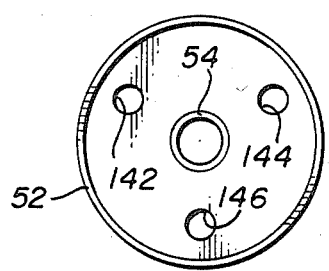
FIG. 13 is bottom view of the closure or retainer means illustrating three ports spaced from the center viewing port, two of which indicate whether or not proper washing has occurred and the third of which represents a control test point which confirms the reaction that takes place in the center viewing port.

Thus the embodiment shown in FIG. 12 provides for a quick determination of whether or not proper washing has occurred while embodiment in FIG. 13 not only provides the determination of proper washing but also provides a control standard to confirm whether or not the reaction indicated in port 54 is truly a positive or a negative test and whether the proper assay steps have been performed.

Thus there has been disclosed an improved diagnostic device for analyte assay which includes a cylindrical body portion and a removable cap portion having a liquid input means that can include a variable diameter liquid discharge aperture. In addition, the cap portion may have a filter membrane within the liquid input portion thereof if desired or may be associated with a pre-mixing container that has a removable cap thereon, a filter internally thereof and a bottom portion which has a frangible membrane thereover for sealing the container. Thus pre-mixing may occur in the container. A puncturing device is associated with the test device and may be placed in the lower portion of the liquid input means with the point downward for storage whereby the pre-mixing container may also be placed in the liquid means without the puncturing device rupturing the frangible lower seal thereof. When the device is ready to be used, the puncturing device can be removed and replaced in the liquid input means with the point facing upwardly and then after the liquids have been pre-mixed in the pre-mixing container, the container can be placed in the liquid input receiving portion of the removable cap whereby the point of the puncturing device ruptures the frangible seal and allows the liquid in the pre-mixing container to be funneled by the discharge aperture onto the reaction zone of the filter. Thus an improved diagnostic device and associated pre-mixing container have been disclosed.

While the invention has been described in connection with a preferred embodiment, it is not intended to limit the scope of the invention to the particular form set forth, but, on the contrary, it is intended to cover such alternatives, modifications and equivalents as may be included within the spirit and scope of the invention as defined by the appended claims.

I claim:

1. In a device for testing for the presence of an analyte in a liquid and having an elongated liquid input means with a receiving inlet and a discharge aperture, said receiving inlet being larger than said discharge aperture, a filter means positioned below said liquid input means and having a viewable reaction zone and at least one peripheral zone associated with said reaction zone, absorbent means associated with only said peripheral zone to draw liquid from said reaction zone to said peripheral zone and retainer means for holding such filter means in position below said liquid input means such that said reaction zone receives liquid funneled from said receiving inlet to said discharge aperture, the improvement comprising:
    a. a body portion having an opening in both the top and bottom thereof, said retaining means cooperating with said bottom opening to hold said filter means in said body portion below said liquid input means and to hold said absorbent means in association with only said peripheral zone of said filter, and
    b. a cap for removable attachment to said top opening of said cylindrical body portion, said cap having said elongated liquid input means projecting therefrom such that when said cap is attached to said body portion, said liquid input means discharge aperture is in contact with said filter means reaction zone for enabling liquid poured into said receiving inlet to be funneled for localized discharge only on said reaction zone.

2. A device as in claim 1 further including:
    a. said cap having means thereon for attaching said cap to said top opening of said body portion, and
    b. said cap projecting liquid input means having any one of variable size discharge apertures thereby enabling selected tests to be performed with said device by selecting a cap with the proper size discharge aperture for a particular test.

3. A device as in claim 2 further including:
    a. a reaction container for removable insertion in said liquid input means receiving inlet, and
    b. a support flange extending radially and circumferentially about the exterior of said container for resting on said cap when said container is inserted in said cap elongated liquid input means receiving inlet thereby holding said container in a secure relationship in said receiving inlet.

4. A device as in claim 3 wherein said container further includes:
    a. an upper opening,
    b. a closure for securely sealing said upper opening,
    c. a lower opening, and
    d. a frangible membrane formed over and securely sealing said lower opening.

5. A device as in claim 4 wherein said container further includes a flexible conector attaching said closure means to said container in proximity to said upper opening such that said closure means stays attached to said container.

6. A device as in claim 5 wherein said container further includes:
    a. a circumferential ledge formed on the inside of said container at a distance removed from both said upper opening and said sealed lowered opening, and
    b. a membrane positioned on and held by said circumferential ledge for acting as a filter for any liquid poured in said upper opening of said container and allowing only liquid to pass therethrough.

7. A device as in claim 6 further including puncture means associated with said elongated liquid input means for rupturing said frangible membrane in said container when said container is inserted in said receiving inlet of said cap.

8. A device as in claim 7 further including:
    a. a conical shape surface coupling the bottom of said receiving inlet with said discharge aperture to funnel liquids thereto, and
    b. said puncture means having openings therein and having a pointed shape corresponding to said conical surface whereby said point is placed downward in said funnel for storage and upwards in the bottom of said receiving inlet for rupturing said membrane in said container to allow fluids therein to discharge on said filter reaction zone.

9. A device as in claim 8 wherein said puncture means comprises:
    a. a base, and
    b. a plurality of spaced arms extending from said base and joining to form a conical shape having a single point for rupturing said frangible membrane, the spaces between said arms passing liquid therethrough when said membrane is ruptured.

10. A device for testing for the presence of an analyte in a liquid comprising:
   a. a body portion having upper and lower open ends,
   b. a filter positioned in said body portion and having a reaction zone and at least one peripheral zone associated with said reaction zone,
   c. absorbent means in said body portion and associated with only said peripheral zone of said filter for drawing liquid from said reaction zone to said peripheral zone,
   d. a liquid input means removably attached to said upper opening of said body portion, said liquid input means having a liquid receiving inlet and a liquid discharge aperture projecting therefrom such that when said liquid input means is attached to said body portion, said liquid discharge aperture is in contact with said filter means reaction zone for enabling liquid poured in said liquid receiving inlet to be funneled for localized discharge only on said reaction zone, and
   e. retainer means associated with said body portion for holding said filter means below said liquid input means discharge aperture such that said reaction zone receives liquid therefrom.

11. A device as in claim 10 wherein said liquid input means comprises:
   a. a cap having means thereon for attaching said cap to said body portion top opening,
   b. said liquid receiving inlet and said discharge aperture being integrally formed with and projecting from said cap to the interior of said body portion when said cap is attached to the top opening thereof, and
   c. said discharge aperture being any of a plurality of variable sizes thereby enabling selected tests to be performed with said device by selecting a cap with the proper size discharge aperture for a particular test.

12. A device as in claim 10 further comprising:
   a. a first viewing port in said retainer means in superimposed relationship with said reaction zone of said filter whereby said reaction zone may be viewed from the bottom of said device, and
   b. at least one additional viewing port in said retainer means spaced apart from said first viewing port and located in said peripheral zone of said filter whereby if improper washing occurs to create a false reaction in said first viewing port, said false reaction will also occur in said additional port thereby allowing said false reaction to be detected.

13. A device as in claim 10 further comprising:
   a. a central viewing port in said retaining means in superimposed relationship with said reaction zone of said filter for viewing said reaction from the bottom of said device,
   b. a second viewing port in said retaining means spaced apart from said first viewing port and in abutting relationship with peripheral zone of said filter for determining if improper washing occurs,
   c. a third viewing port in said retaining means spaced apart from said first and second viewing ports and in abutting relationship with said peripheral zone of said filter, and
   d. a control standard associated with said filter within the area of said third viewing port whereby the desired reaction will be indicated in the third viewing port when the proper analytes have been added thereby enabling confirmation of the reaction or lack of reaction in the first viewing zone.

14. In a method for testing for the presence of an analyte in a liquid by providing an elongated liquid input means with a receiving inlet and a discharge inlet, said receiving inlet being larger than said discharge aperture, positioning a filter means below said liquid input means with a viewable reaction zone and at least one peripheral zone associated with said reaction zone, associating absorbent means only with said peripheral zone to draw liquid from said reaction zone to said peripheral zone and holding said filter means in position below said liquid means with a retainer means such that said reaction zone receives liquid funneled from said receiving inlet to said discharge aperture, the improvement comprising the steps of:
   a. providing a body portion having an opening in both the top and bottom thereof, said retainer means cooperating with said bottom opening to hold said filter means in said body portion below said liquid input means and to hold said absorbent means in association with only said peripheral zone, and
   b. removably attaching a cap to said top opening of said cylindrical body portion, said cap having said elongated liquid input means projecting therefrom such that when said cap is attached to said body portion, said liquid means discharge aperture is in contact with said filter means reaction zone for enabling liquid poured into said inlet to be funneled for localized discharge only on said reaction zone.

15. The method as in claim 12 further comprising the steps of:
   a. providing means on said cap for attaching said cap to said top opening of said body portion,
   b. providing any one of variable size discharge apertures in said projecting liquid input means of said cap, and
   c. selecting a cap with the proper size discharge aperture for a particular test thereby matching a particular cap with a particular test.

16. The method as in claim 15 further including the steps of:
   a. removably inserting a reaction reservoir container in said liquid input means receiving inlet, and
   b. radially and circumferentially extending a support flange about the exterior of said container for resting on said cap when said container is inserted in said cap elongated liquid input means inlet thereby holding said container in a secure relationship in said receiving inlet.

17. A method as in claim 16 further including the steps of:
   a. forming an upper opening in said container,
   b. forming a closure for securely sealing said upper opening,
   c. forming a lower opening in said container, and
   d. securely sealing said lower opening with a frangible membrane.

18. A method as in claim 17 further including the step of attaching said closure means to said container in proximity to said upper opening with a flexible connector such that said closure means stays attached to said container.

19. A method as in claim 18 further including the steps of:

a. forming a circumferential ledge on the inside of said container at a distance removed from both said upper opening and said sealed lower opening, and b. positioning a membrane on said circumferential ledge for acting as a filter for any liquid poured in said upper opening of said container and allowing only liquid to pass therethrough.

20. A method as in claim 19 further including the step of associating puncture means with said elongated liquid input means for rupturing said frangible membrane in said container when said container is inserted in said receiving inlet of said cap.

21. A method as in claim 20 further including the steps of:

a. coupling the bottom of said receiving inlet with said discharge aperture with a conical shaped surface to funnel liquids thereto, and b. forming said puncture means with openings therein and a pointed shape corresponding to said conical surface whereby said point is placed downward in said funnel for storage and upward in the bottom of said receiving inlet for rupturing said membrane in said container to allow fluids therein to discharge on said filter reaction zone.

22. A method as in claim 21 further comprising the steps of:

a. forming said puncture means with a base, and b. extending a plurality of spaced arms from said base and joining said arms to form a conical shape having a single point for rupturing said frangible membrane, the spaces between said arms passing liquid therethrough.

23. A method for testing for the presence of an analyte in a liquid comprising the steps of:

a. forming a body portion having upper and lower open ends, b. positioning a filter in said body portion with a reaction zone and at least one peripheral zone associated with said reaction zone, c. associating absorbent means in said body portion with only said peripheral zone of said filter for drawing liquid from said reaction zone to said peripheral zone, d. removably attaching a liquid input means to said upper opening of said body portion, said liquid input means having a liquid receiving inlet and a liquid discharge aperture projecting therefrom such that when said liquid input means is attached to said body portion, said liquid discharge aperture is in contact with said filter means reaction zone for enabling liquid poured in said liquid receiving inlet to be funneled for localized discharge only on said reaction zone, and e. associating retainer means with said body portion for holding said filter means below said liquid input means discharge aperture such that said reaction zone receives liquid therefrom.

24. A method as in claim 23 further comprising the steps of:

a. attaching said cap to said body portion with attaching means, b. integrally forming said liquid input means with said cap so as to project said liquid input means into the interior of said body portion when said cap is attached thereto, and c. forming said discharge aperture of any one of a plurality of variable sizes thereby enabling selected tests to be performed with said device by selecting a cap with the proper sized discharge aperture for a particular test.

25. A method as in claim 21 further comprising the steps of:

a. forming a first viewing port in said retainer means in superimposed relationship with said reaction zone of said filter for viewing said reaction zone from the bottom of said body portion, and b. forming at least a second viewing port in said retainer means spaced apart from said first viewing port and in superimposed relationship with said peripheral zone of said filter whereby if improper washing occurs to create a false reaction in said first viewing port, said false reaction is also present in said second viewing port thereby allowing said false reaction to be detected.

26. A method as in claim 21 further comprising the steps of:

a. forming a central viewing port in said retainer means in superimposed relationship with said reaction zone of said filter for viewing said reaction from the bottom of said body portion, b. forming a second viewing port in said retainer means spaced apart from said first viewing port and in superimposed relationship with said peripheral zone of said filter whereby if improper washing creates a false positive reaction in said first viewing zone, said false positive reaction is also present in said second viewing port thereby allowing said false reaction to be detected, c. forming a third viewing port in said retainer means spaced apart from said first and second viewing ports and in superimposed relationship with the peripheral zone of said filter, and d. associating a control standard in said peripheral zone of said filter in said area superimposed by said third viewing port whereby a negative or positive reaction in said first viewing port is confirmed by a positive reaction taken into place in said third viewing port.

* * * * *

UNITED STATES PATENT AND TRADEMARK OFFICE
CERTIFICATE OF CORRECTION

PATENT NO. : 4,693,834
DATED : September 15, 1987
INVENTOR(S) : Hossom

It is certified that error appears in the above-identified patent and that said Letters Patent are hereby corrected as shown below:

Claim 5 (column 16, line 33) "conector" should read --connector--.

Claim 15 (column 18, line 34) cancel "12" and substitute therefor --14--.

Claim 16 (column 18, line 51) after "means" insert --receiving--.

Signed and Sealed this

Nineteenth Day of January, 1988

*Attest:*

DONALD J. QUIGG

*Attesting Officer*        *Commissioner of Patents and Trademarks*